United States Patent
Gerardo

(10) Patent No.: US 8,715,328 B2
(45) Date of Patent: May 6, 2014

(54) MONOCULAR LIGHT SOURCE POSITIONING DEVICE AND METHOD FOR STIMULATING PHOTONEURONIC RESPONSE

(76) Inventor: Ernesto Gerardo, Brecksville, OH (US)

(*) Notice: Subject to any disclaimer, the term of this patent is extended or adjusted under 35 U.S.C. 154(b) by 151 days.

(21) Appl. No.: 12/958,618

(22) Filed: Dec. 2, 2010

(65) Prior Publication Data

US 2011/0130810 A1 Jun. 2, 2011

Related U.S. Application Data

(60) Provisional application No. 61/265,960, filed on Dec. 2, 2009.

(51) Int. Cl.
*A61N 5/06* (2006.01)
(52) U.S. Cl.
USPC ............................. 607/91; 607/88; 607/90
(58) Field of Classification Search
CPC .............. A61N 5/0614; A61N 2005/0636; A61N 5/06; A61N 2005/0655; A61N 2005/0652
USPC ............................................ 607/91; 351/123
See application file for complete search history.

(56) References Cited

U.S. PATENT DOCUMENTS

| | | | |
|---|---|---|---|
| 5,447,528 A * | 9/1995 | Gerardo | 607/88 |
| 5,923,398 A | 7/1999 | Goldman | |
| 6,053,936 A | 4/2000 | Koyama et al. | |
| 6,212,020 B1 * | 4/2001 | Ahlgren et al. | 359/815 |
| 6,235,046 B1 | 5/2001 | Gerdt | |
| 6,350,275 B1 | 2/2002 | Vreman et al. | |
| 8,538,056 B2 * | 9/2013 | Ishibashi et al. | 381/330 |
| 2005/0002539 A1 * | 1/2005 | Nielsen | 381/312 |
| 2007/0046889 A1 * | 3/2007 | Miller et al. | 351/62 |
| 2008/0144877 A1 * | 6/2008 | Ham et al. | 381/379 |
| 2009/0161064 A1 * | 6/2009 | Rabbi | 351/123 |
| 2012/0237068 A1 * | 9/2012 | Fretz et al. | 381/330 |
| 2012/0321114 A1 * | 12/2012 | Ishibashi et al. | 381/330 |

FOREIGN PATENT DOCUMENTS

WO   WO 2006109969 A1 * 10/2006

* cited by examiner

Primary Examiner — Gary Jackson
Assistant Examiner — John R Downey
(74) Attorney, Agent, or Firm — John R. Benefiel

(57) ABSTRACT

A monocular light source positioning device includes a support member which held on the head of a user to hold an elongated readily bendable but self supporting element having a light source effective to stimulate a photo-endocrine response attached at a free end thereof positioned over or in front of only one eye of the person to provide a method of stimulating a photoendocrine response without interfering with the principal field of view of the user.

3 Claims, 2 Drawing Sheets

US 8,715,328 B2

MONOCULAR LIGHT SOURCE POSITIONING DEVICE AND METHOD FOR STIMULATING PHOTONEURONIC RESPONSE

CROSS REFERENCE TO RELATED APPLICATIONS

This application claims the benefit of U.S. provisional 61/265,960 filed on Dec. 2, 2009, incorporated herein by reference.

BACKGROUND OF THE INVENTION

This invention concerns the use of light to stimulate a photo-endocrine response within the human optic-endocrine axis. This response may be used to treat numerous conditions, such as Seasonal Affective Disorder, Jet Lag, and many other conditions now believed to respond to light therapy. These conditions are thought to involve a failure of person's body to maintain a proper circadian rhythm which is regulated by daily exposure of the retinas to light of a specific color wavelength range. This failure can cause undesirable mood disorders and many other physical conditions. Various devices have been developed for treating these conditions, including light boxes before which a person stands for particular time periods on a daily basis.

The desirability of allowing a user to move about and conduct normal activities while receiving treatment has led to the development of portable devices such as light sources mounted to the underside of the bill of a cap as described and claimed in the present inventor's prior U.S. Pat. Nos. 5,447, 528 and 5,293,375. Other devices include mounting of light sources to spectacle frames such as shown in U.S. Pat. Nos. 6,350,275; 5,923,398; and 6,235,046, and other head mounted light sources such as shown in U.S. Pat. No. 6,053, 936.

It is the object of the present invention to provide such a device which further reduces the interference such treatment imposes on the normal activities of a person being treated.

SUMMARY OF THE INVENTION

The above recited object and other objects which will be understood by one skilled in the art upon a reading of the following specification and claims are achieved by a monocular photoneuronic device which includes a support member held on the head of a user as by being engaged with at least one ear of a wearer and includes a housing supported thereby adapted to receive a battery and associate electronics. An elongated easily bendable but self supporting element is connected at one end to the housing and is of a length able to be extended forwardly to position a light source attached to the other end thereof in front of or just above one eye of the wearer. The position of the light source can be adjusted by the wearer to achieve a desired comfort level while causing a sufficient light intensity to enter the eye. The light source may be a single narrow beam cyan LED mounted within a reflector body, oriented so as to direct light into the one eye. The light emitted by the light source is preferably of a wavelength between approximately 420 mm and 520 mm and of sufficient intensity to effectively stimulate a photoendocrine response.

As an example, an intensity of 500 lux or greater may be directed into the person's eye although lower intensities may also create some stimulative effect.

In a first embodiment, the housing is held by a U shaped support member extending around the back of the wearer's head and retained thereon by a pair of ear clips, the battery housing located thereby at the back of the head of the wearer.

In a second embodiment, a bendable, a single curved ear grip support member may be configured to fit around the antihelical fold within the wearer's ear to provide support for the housing.

In the second embodiment, a connector extends from the support member to a battery/electronics housing positioned behind the person's ear.

In both embodiments, an easily bendable but self supporting elongated element holds the simulative light source at a distal end thereof. The light source is positioned as desired over or in front of one eye by bending of the elongated element as necessary.

Both embodiments provide a support for a single light source positioned in front of one eye while leaving the other eye completely clear of any structure so as to not interfere with the wearer's principal field of view.

The devices of both embodiments are simpler and more compact than prior such devices.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 1:
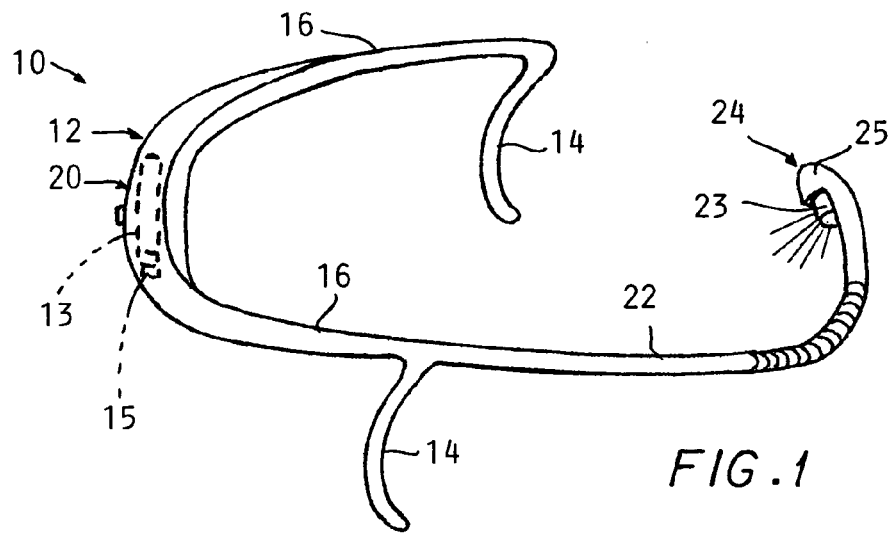
FIG. 1 is a pictorial view of a first embodiment of a monocular light source positioning device according to the present invention.
Figure 2:
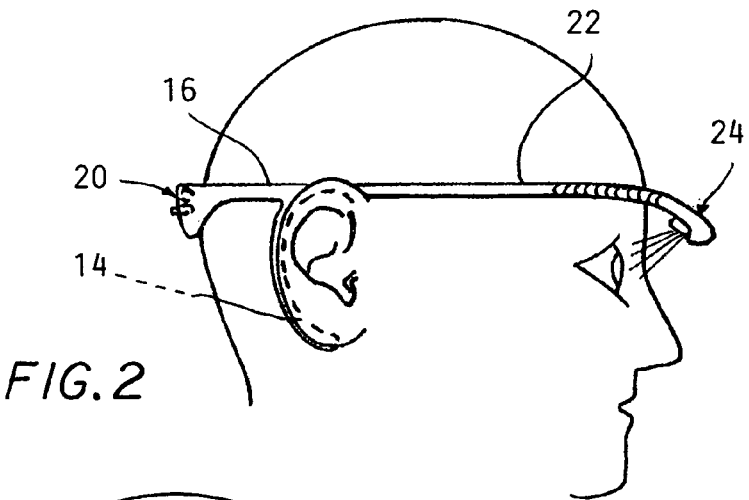
FIG. 2 is a side view of a person wearing the monocular light source positioning device shown in FIG. 1 with a light source located above one eye of the wearer.
Figure 3:
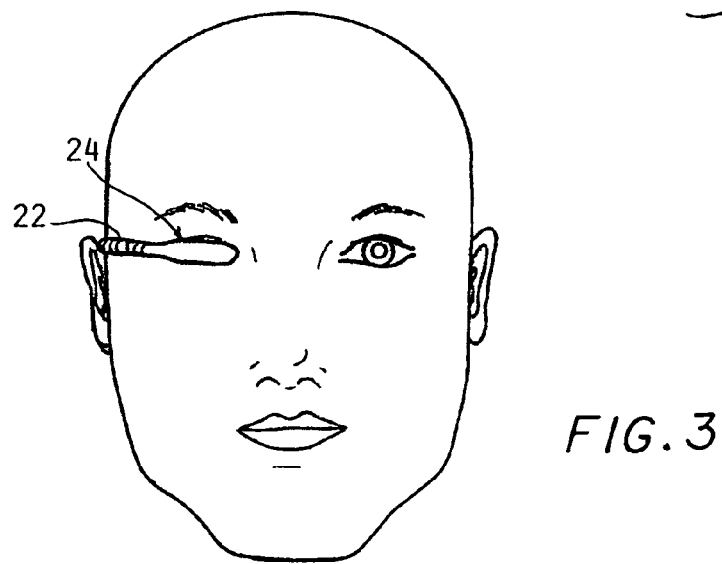
FIG. 3 is a front view of a person wearing the monocular light source positioning device shown in FIG. 1 with the light source positioned directly in front of one eye of a wearer.

Referring to the drawings and in particular FIGS. 1-3, a first embodiment of a monocular light source treatment device 10 is shown.

A U-shaped support member 12 has a curved ear clip 14 on each of the inwardly turned ends of each leg 16 of the support member 12 (FIG. 1). Hooking of one clip 14 behind each ear secures the support member 12 in position extending around the rear of a wearer's head as seen in FIG. 2.

The rear of U-shaped member 12 mounts housing 20 containing a battery 13 and associated electronics 15. An on-off switch 21 is also provided on the housing 20. These components may be of conventional design, as suitable components are readily available.

Projecting from one side of the support member 12 is an easily bendable but self supporting elongated light support element 22 which supports and also transmits power from the battery 13 to a light source 24. This element may comprise bendable electrical cables encased in an insulating plastic.

The light source 24 preferably comprises an LED 23 mounted in an enclosing shell 25 having a directional reflector therein.

Bendable element 22 provides a "goose neck" function enabling manually adjustable positioning of the light source 24 relative to one eye only of the wearer, such as above the eye and angled down towards the eye as seen in FIG. 2. The cable 22 is stiff enough to maintain any such adjusted position.

Figure 4:
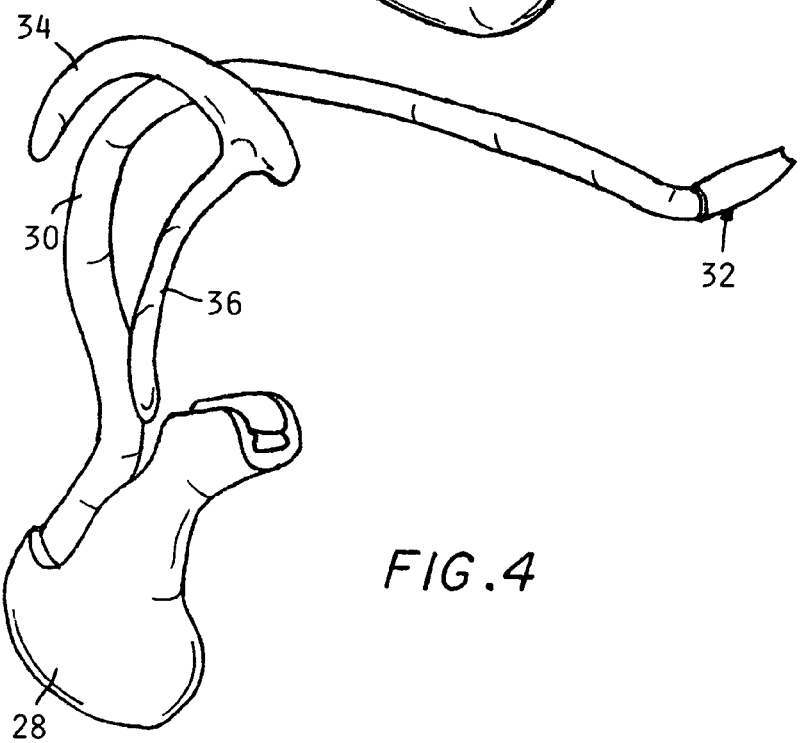
FIG. 4 is a pictorial view of a second embodiment of a monocular light source positioning device according to the present invention.

Since only one eye is illuminated according to the concept of the invention, the light source 24 can be positioned directly in front of one of the person's eyes as shown in FIGS. 3 and 4 without interfering with the wearer's principal field of view. Mirror versions of the device will allow for positioning the light over either the left or right eye.

This will create a more intense stimulation of the retina of one eye.

The light source 24 is powered and controlled by the conventional rechargeable battery 13, which with control electronics 15 provided for intensity adjustment and an on/off switch 21 may be contained in the housing 20.

As is now well known in the art, effective light therapy by stimulating a photoendocrine response is best achieved by blue/violet and green light (wavelengths ranging between approximately 420 nm to 520 nm).

Such light may be advantageously produced by a single narrow beam cyan LED (such as from TT Electronics, PN ORLGCOC6B9) with a peak emission wavelength of 505 nm.

The light intensity should preferably be at least 500 lux although lower intensities may produce some stimulative photoendocrine response, which is easily achievable with the LED positioned at a distance of approximately one inch from the wearer's eye.

Figure 6:
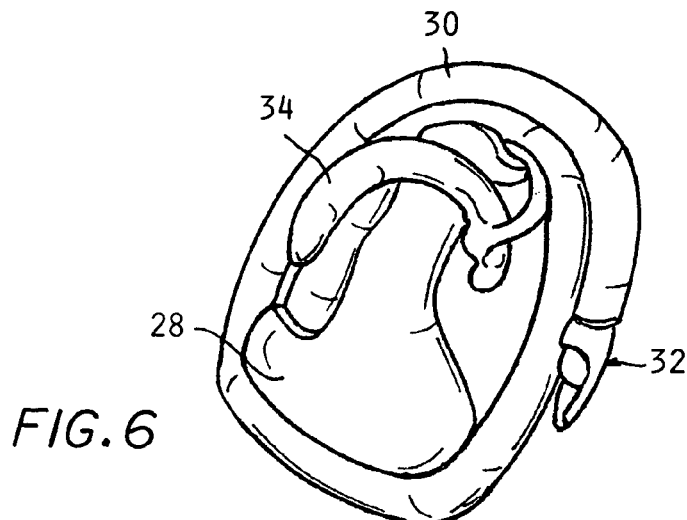
FIG. 6 is a pictorial view of the device shown in FIG. 4 wrapped up on itself for compact storage.
Figure 5:
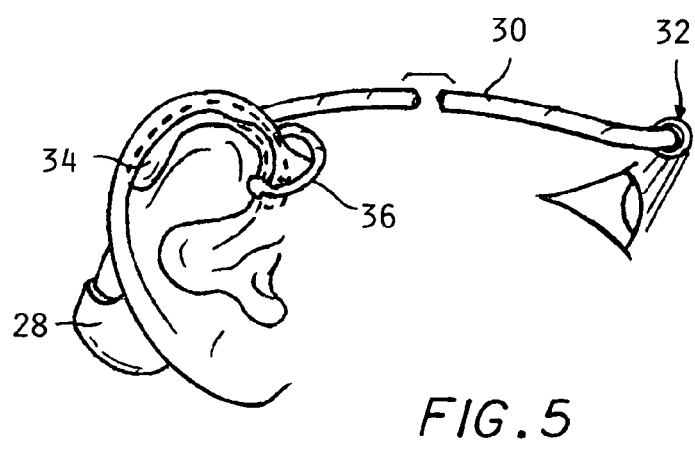
FIG. 5 is a pictorial view of the device shown in FIG. 4 being worn by a user.

Referring to FIGS. 4-6, a second embodiment of a monocular light source positioning device 26 is shown which is supported by a single ear of a wearer.

Device 26 comprises a molded plastic assemblage including a bulbous housing 28 having an elongated readily bendable light source support element 30 projecting therefrom. A compact LED assembly 32 is mounted at the free end thereof to be readily positionable by bending element 30 as necessary.

A support piece 34 is attached by a second elongated element 30 to the elongated light source support element 30.

The support piece 34 (which may be bendable) is fit around the antihelix fold of the wearer's ear as indicated in FIG. 5.

This allows the housing 28 to be held behind the wearer's ear with the element 30 extending alongside his or her head and bent around to a position above the eye (or directly in front of the eye as shown in FIG. 3).

Accordingly, the compact devices described are effective in producing a photoendocrine response without interfering with the wearer's principal field of vision even when the light source is positioned directly in front of one eye.

Thus light therapy can be undergone without a substantial interference with the normal activities of a wearer.

The invention claimed is:

1. A monocular light source positioning device for use in administering light therapy onto a single eye of a wearer, comprising:
   a support member adapted to be held on the head of a human wearer by engagement with only a single ear of the wearer;
   a housing connected with said support member receiving a battery and associated electronics;
   an elongated readily bendable but self supporting first bendable element connected to said housing and of a length able to position a free end thereof at a point forward of one eye of the wearer;
   said support member comprising an elongated deformable curved piece configured to extend along in conformity to the antihelix fold within a wearer's ear so as to be held therein, said support member being connected to said first bendable elongated element by an intervening second elongated bendable element so as to thereby solely support said housing by emplacement of said elongated curved piece along said antihelix fold within a wearer's ear;
   a light source mounted to said free end of said bendable element and electrically connected to said battery and electronic controls thereby;
   said light source emitting light of a wavelength and intensity effective to stimulate a photoendocrine response when positioned adjacent one eye of the wearer to cause said emitted light to enter said one eye;
   whereby the wearer can receive such stimulation while wearing said device by positioning said light source forward and aligned with a single eye of the wearer by bending said elongated first element as necessary while leaving the other eye with an unobstructed view.

2. The device according to claim 1 wherein said light source includes a single LED emitting light in the approximate wavelength range of 420 to 520 nm.

3. The device according to claim 1 wherein said first bendable device is configured to locate said light source directly in front of the wearer's one eye.

* * * * *